United States Patent [19]
Sato et al.

[11] Patent Number: 5,478,945
[45] Date of Patent: Dec. 26, 1995

[54] THIAZOLINE DERIVATIVES

[75] Inventors: Masakazu Sato, Konosu; Akira Manaka, Ageo; Keiko Takahashi, Tokyo; Yutaka Kawashima, Tatebayashi; Katsuo Hatayama, Omiya, all of Japan

[73] Assignee: Taisho Pharmaceutical Co., Ltd., Tokyo, Japan

[21] Appl. No.: 371,141

[22] Filed: Jan. 11, 1995

Related U.S. Application Data

[60] Continuation-in-part of PCT/JP93/00937, Jul. 8, 1993.

[30] Foreign Application Priority Data

| Jul. 15, 1992 | [JP] | Japan | 4-188335 |
| Nov. 27, 1992 | [JP] | Japan | 4-318402 |
| Jan. 14, 1994 | [JP] | Japan | 6-002588 |
| Jan. 14, 1994 | [JP] | Japan | 6-002722 |

[51] Int. Cl.$^6$ ................................. C07D 277/56
[52] U.S. Cl. .................. 548/195; 544/58.7; 544/133; 544/364; 544/360; 546/19; 546/209; 546/280
[58] Field of Search .................. 548/195; 544/58.7, 544/133, 360, 364; 546/19, 209, 280

[56] References Cited

U.S. PATENT DOCUMENTS 5,039,805  8/1991  Alig et al. .

FOREIGN PATENT DOCUMENTS

| 0261503 | 3/1988 | European Pat. Off. . |
| 2-50148 | 5/1988 | Japan . |
| 223543 | 1/1989 | Japan . |

*Primary Examiner*—Robert Gerstl
*Attorney, Agent, or Firm*—Oblon, Spivak, McClelland, Maier, & Neustadt

[57] ABSTRACT

A thiazoline derivative represented by the formula:

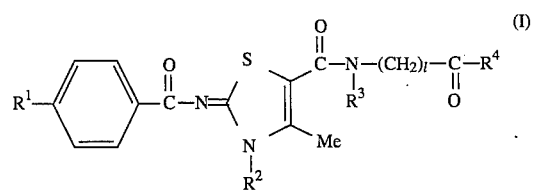

[wherein $R^1$ is cyano, carbamoyl, thiocarbamoyl, morpholinothiocarbonyl, alkylthioimidoyl, amidino, substituted amidino or imidazolin-2-yl, $R^2$ is alkyl or aralkyl, $R^3$ is hydrogen or alkyl, $R^4$ is hydroxyl, alkoxy, substituted alkoxy or amino, l is an integer of 1 to 5] and salts thereof have fibrinogen receptor antagonism and cell adhesion factor antagonism, and are useful as therapeutic agents for ischemic diseases and atherosclerosis diseases, and metastasis inhibitory agents of tumors.

1 Claim, No Drawings

THIAZOLINE DERIVATIVES

CROSS-REFERENCE TO THE RELATED APPLICATION

This is a continuation-in-part application of PCT/JP93/00937 filed on Jul. 8, 1993, in Japan, the content of which is herein incorporated by reference.

TECHNICAL FIELD

The present invention relates to thiazoline derivatives, and more particularly novel thiazoline derivatives having fibrinogen receptor antagonism and cell adhesion factor antagonism.

BACKGROUND ART

Blood platelets are considered to bind each other via fibrinogen and aggregate as a result of the appearance of the binding site of fibrinogen on the blood platelet membrane glycoprotein GPIIb/IIIa complex caused by stimulation of various blood platelet aggregation-induced substances. Therefore, the compounds having the antagonism against fibrinogen receptor are expected to have the inhibitory action of blood platelet aggregation. Among the known compounds having the inhibitory action of blood platelet aggregation are peptide derivatives such as Arg-Gly-Asp-Ser containing Arg-Gly-Asp (hereinafter referred to as RGDS) which is considered to be a binding site of fibrinogen receptor [Thrombosis Res., vol. 56, No. 6, page 687 (1989)] and compounds having an amidino group in the intermolecular (described in Japanese Patent Kokai 2-223543).

However, the above compounds are insufficiently effective.

An object of the present invention is to provide compounds having excellent fibrinogen receptor antagonism and cell adhesion factor antagonism, i.e., excellent inhibitory agents for blood platelet aggregation.

DISCLOSURE OF THE INVENTION

As a result of various researches, the present inventors have found novel thiazoline derivatives having fibrinogen receptor antagonism and cell adhesion factor antagonism, and have accomplished the present invention.

The present invention is a thiazoline derivative represented by the formula:

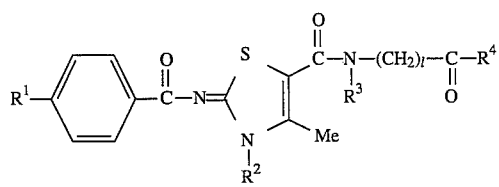

[wherein $R^1$ is
(i) a cyano group,
(ii) a carbamoyl group,
(iii) a thiocarbamoyl group,
(iv) a morpholinothiocarbonyl group,
(v) an alkylthioimidoyl group having 2 to 7 carbon atoms, (vi) a group represented by the formula:

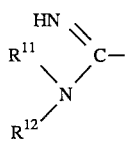

(wherein $R^{11}$ and $R^{12}$ are each a hydrogen atom, an alkyl group having 1 to 6 carbon atoms, an alkoxycarbonyl group having 2 to 7 carbon atoms, a cycloalkyl group having 4 to 8 carbon atoms, a phenyl group, a phenyl group substituted by an alkyl group having 1 to 4 carbon atoms, an alkoxy group having 1 to 4 carbon atoms or a halogen atom, an aralkyl group, or an aralkyl group substituted by an alkyl group having 1 to 4 carbon atoms, an alkoxy group having 1 to 4 carbon atoms, a trifluoromethyl group or a halogen atom), (vii) a group represented by the formula:

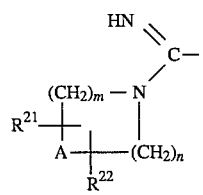

(wherein $R^{21}$ and $R^{22}$ are each a hydrogen atom or an alkyl group having 1 to 6 carbon atoms, m and n are each an integer of 1 to 3, and A is a methylene group, a carbonyl group, an ethylenedioxymethylene group, an oxygen atom, a sulfur atom, a sulfinyl group, a sulfonyl group or a group represented by the formula:
(wherein $R^{23}$ is a hydrogen atom, an alkyl group having 1 to 6 carbon atoms, a formyl group, an alkanoyl group having 2 to 7 carbon atoms, a phenyl group, a phenyl group substituted by an alkyl group having 1 to 6 carbon atoms, an alkoxy group having 1 to 6 carbon atoms, a nitro group, an alkanoyl group having 2 to 7 carbon atoms, a halogen atom or a trifluoromethyl group, a pyridyl group or a benzyl group)), or (viii) an imidazolin-2-yl group, $R^2$ is an alkyl group having 1 to 10 carbon atoms or an aralkyl group, $R^3$ is a hydrogen atom or an alkyl group having 1 to 4 carbon atoms, $R^4$ is a hydroxyl group, an alkoxy group having 1 to 6 carbon atoms, an alkoxy group having 1 to 6 carbon atoms substituted by a phenyl group, a pyridyl group, a morpholino group, an alkanoyloxy group having 2 to 7 carbon atoms, an alkoxy group having 1 to 6 carbon atoms, an N,N-dialkylaminocarbonyl group or an N,N-dialkylamino group or an amino group, and l is an integer of 1 to 5] and a salt thereof.

In the present invention, the alkyl group and the alkyl moieties of the alkoxy group, the alkoxycarbonyl group, the alkanoyl group, the alkanoyloxy group, an N,N-dialkylamino group, an N,N-dialkylaminocarbonyl group and alkylthioimidoyl group are those which are straight or branched. The aralkyl group refers to an alkyl group having 1 to 3 carbon atoms substituted by an aryl group (e.g. a phenyl group, a naphthyl group or a pyridyl group) at the end thereof such as, for example, a benzyl group, a phenethyl group, a naphthylmethyl group, a pyridylmethyl group or a pyridylethyl group. The halogen atom refers to a fluorine atom, a chlorine atom, a bromine atom and an iodine atom.

The salt of the compounds of Formula (I) refers to salts with alkali metals, alkalline earth metals, ammonia, alkylamines, mineral acids, carboxylic acids or sulfonic acids such as, for example, sodium salt, potassium salt, calcium salt, ammonium salt, aluminium salt, triethylammonium salt, 1-adamantanammonium salt, hydrochloride, hydrobromide, hydroiodide, sulfate, nitrate, phosphate, acetate, fumarate, malate, methanesulfonate, succinate, butyrate, tartrate, citrate, gallate, maleate, caproate, valerate, propionate and methylsulfate.

Among the preferred compounds of the present invention are the compounds of Formula (I) wherein $R^1$ is a group of Formula (II) or (III), $R^3$ is a hydrogen atom, l is 2, and $R^4$ is a hydroxyl group.

The compounds of the present invention can be prepared, for example, by the following methods.

First, a compound represented by the formula:

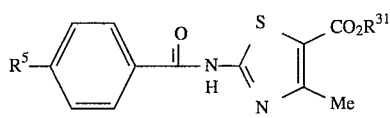

(wherein $R^5$ is a cyano group or a morpholinothiocarbonyl group as defined for $R^1$, and $R^{31}$ is a lower alkyl group, a benzyl group or a 2-cyanoethyl group) is reacted with a reagent (e.g. methyl iodide or benzyl chloride) represented by the formula:

$R^2$—X (wherein $R^2$ is as defined above, and X is a halogen atom) in the presence of a base to lead to a compound represented by the formula:

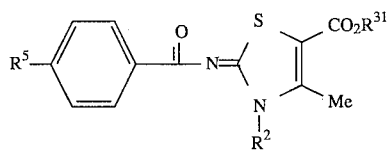

(wherein $R^2$, $R^5$ and $R^{31}$ are as defined above).

The compound of Formula (b) wherein $R^2$ is other than an aralkyl group can also be obtained by a reaction of an alkylating agent such as a dialkyl sulfate (e.g. dimethyl sulfate) represented by the formula:

$R^6{}_2$—SO$_4$ (wherein $R^6$ is $R^2$ other than an aralkyl group), or a sulfonate (e.g. methyl methanesulfonate ) represented by the formula:

$R^{32}SO_3R^6$ (wherein $R^{32}$ is an alkyl group or an aryl group, and $R^6$ is as defined above) with a compound of Formula (a) in the presence of a base.

Next, the ester moiety of the compound of Formula (b) is hydrolyzed by using a conventional method to lead to a compound represented by the formula:

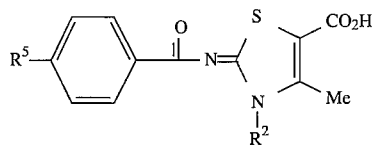

(wherein $R^2$ and $R^5$ are as defined above) or a salt thereof, and reacted using an amine represented by the formula:

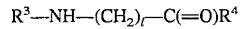

$R^3$—NH—(CH$_2$)$_l$—C(=O)R$^4$ (wherein l, $R^3$ and $R^4$ are as defined above) according to a conventional amide linkage formation method to give a compound of the present invention of Formula (I) wherein $R^1$ is a cyano group or a morpholinothiocarbonyl group, i.e. a compound represented by the formula:

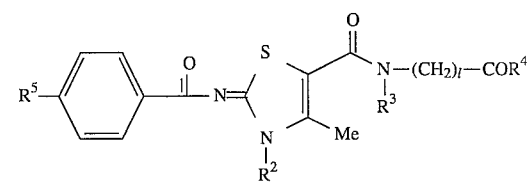

(wherein $R^2$, $R^3$, $R^4$, $R^5$, and l are as defined above).

The compound of the present invention of Formula (d) wherein $R^5$ is a cyano group is subjected, for example, to a reaction with hydrogen sulfide by using a base as a catalyst, a mixture of sodium hydrogen sulfide hydrate and magnesium chloride hydrate, or a reaction with NaBH$_2$S$_3$ to give a compound of the present invention of Formula (I) wherein $R^1$ is a thiocarbamoyl group, i.e. a compound represented by the formula:

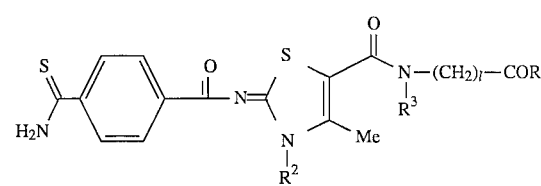

(wherein $R^2$, $R^3$, $R^4$ and l are as defined above). The compound of the present invention of Formula (d) wherein $R^5$ is a cyano group can be reacted with hydrogen peroxide in the presence of a base according to an ordinary method to lead to a compound of the present invention of Formula(I) wherein $R^1$ is a carbamoyl group.

The resulting compound of Formula (e) is treated with a lower alkyl halide represented by the formula:

$R^7$—X (wherein $R^7$ is an alkyl group having 1 to 6 carbon atoms, and X is a halogen atom), a dialkyl sulfate (e.g. dimethyl sulfate) represented by the formula:

$R^7{}_2$—SO$_4$ (wherein $R^7$ is as defined above) or a sulfonate (e.g. methyl methanesulfonate) represented by the formula:

$R^{32}SO_3R^7$ (wherein $R^{32}$ and $R^7$ is as defined above) to give a compound of Formula (I) wherein $R^1$ is an alkylthioimidoyl group having 2 to 7 carbon atoms, or a salt thereof and then reacted with ammonia, a monoalkylamine wherein the alkyl moiety has 1 to 6 carbon atoms, a dialkylamine wherein each of the alkyl moieties has 1 to 6 carbon atoms, a monocycloalkylamine wherein the cycloalkyl moiety has 4 to 8 carbon atoms, aniline, a substituted aniline, an aralkylamine, a substituted aralkylamine, a heterocyclic compound having one or more secondary nitrogen atoms on the ring, 1,2-diaminoethane or a salt thereof to give a compound of Formula (I) wherein $R^1$ is a group of Formula (II) (wherein $R^{11}$ or $R^{12}$ is other than an alkoxycarbonyl group having 2 to 7 carbon atoms), a group of Formula (III) or an imidazolin-2-yl group.

The compound of Formula (I) wherein $R^1$ is a group of Formula (II), at least one of $R^{11}$ and $R^{12}$ is an alkoxycarbonyl group having 2 to 7 carbon atoms can be obtained by a reaction of the compound of Formula (I) wherein $R^1$ is a group of Formula (II), $R^{11}$ is a hydrogen atom, $R^{12}$ is other than an alkoxycarbonyl group having 2 to 7 carbon atoms, i.e. a compound represented by Formula (f):

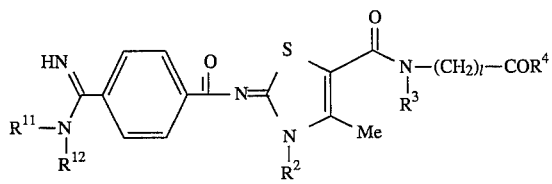

(wherein $R^2$, $R^3$, $R^4$, $R^{11}$, $R^{12}$ and l are as defined above) with a compound represented by the formula:

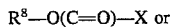

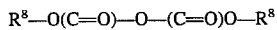

(wherein $R^8$ is an alkyl group having 1 to 6 carbon atoms, and X is a halogen atom) in the presence of a base.

The compound of Formula (I) wherein $R^3$ is an alkyl group having 1 to 4 carbon atoms can be also obtained by following the procedure similar to that of the above introduction of $R^2$ to the compound of Formula (a) using the compound which is obtained by a reaction of the compound of Formula (I) wherein $R^3$ is a hydrogen atom with an alkylating agent such as, for example, a reagent represented by the formula:

(wherein $R^9$ is $R^3$ other than a hydrogen atom, and X is a halogen atom), a compound represented by the formula:

(wherein $R^9$ is as defined above) or a sulfonate (e.g. methyl methanesulfonate) represented by the formula:

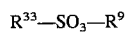

(wherein $R^{33}$ is an alkyl group or an aryl group, and $R^9$ is as defined above) in the presence of a base.

Alternatively, the compound of Formula (I) wherein $R^4$ is a hydroxyl group or a salt thereof can be also prepared by an ester hydrolysis of the compound of Formula (I) wherein $R^4$ is other than a hydroxyl group or an amino group. The ester hydrolysis to be used is an ordinary method such as an alkali treatment or an acid treatment.

The compound of Formula (I) wherein $R^4$ is an amino group can be prepared from the compound of Formula (I) wherein $R^4$ is other than an amino group by an ordinary method for amide-formation from an ester or carboxylic acid such as, for example, by a reaction with ammonia in a solvent.

The compound of Formula (I) wherein $R^4$ is an alkoxy group having 1 to 6 carbon atoms or an alkoxy group having 1 to 6 carbon atoms substituted by a phenyl group, a pyridyl group, a morpholino group, an alkanoyloxy group having 2 to 7 carbon atoms, an alkoxy group having 1 to 4 carbon atoms, an N,N-dialkylaminocarbonyl group or an N,N-dialkylamino group can be prepared by reacting a compound of Formula (I) wherein $R^4$ is a hydroxyl group or a salt thereof with a compound represented by the formula:

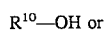

(wherein $R^{10}$ is an alkyl group having 1 to 6 carbon atoms or an alkyl group having 1 to 6 carbon atoms substituted by a phenyl group, a pyridyl group, a morpholino group, an alkanoyloxy group having 2 to 7 carbon atoms, an alkoxy group having 1 to 4 carbon atoms, an N,N-dialkylaminocarbonyl group or an N,N-dialkylamino group, and X is a halogen atom) under ordinary conditions of esterification of a carboxylic acid, for example, by treating with dicyclohexylcarbodiimide in the presence of 4-dimethylaminopyridine. The compound of Formula (I) wherein $R^4$ is an alkoxy group having 1 to 6 carbon atoms or an alkoxy group having 1 to 6 carbon atoms substituted by a phenyl group, a pyridyl group, a morpholino group, an alkanoyloxy group having 2 to 7 carbon atoms, an alkoxy group having 1 to 4 carbon atoms, an N,N-dialkylaminocarbonyl group or an N,N-dialkylamino group can be also prepared by interchanged under ordinary ester interchange conditions, for example, by treating with $R^{10}$—OH (wherein $R^{10}$ is as defined above) in the presence of an acid.

The compound of Formula (I) can be also synthesized from the compound of Formula (I) wherein $R^1$ is a cyano group, for example, by using an ordinary method for conversion of a cyano group to an amidino group via iminochloride or imino ether.

The compound of Formula (I) wherein $R^1$ is an imidazolin-2-yl group can be also prepared by reacting a compound of Formula (I) wherein $R^1$ is a morpholinothiocarbonyl group with an alkyl halide represented by the formula:

(wherein $R^{10}$ is an alkyl group, and X is a halogen atom), and reacting the resulting compound with 1,2-diaminoethane or a salt thereof.

Furthermore, the compound of Formula (I) wherein $R^1$ is a group of Formula (III) can be also prepared as follows: A terephthalaldehydic acid ester as a starting material is reacted with a cyclic secondary amine represented by the formula:

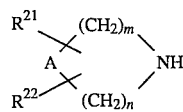

(wherein $R^{21}$, $R^{22}$, A, m and n are as defined above) in the presence of sulfur in a solvent or without solvent under heating to give a compound represented by the formula:

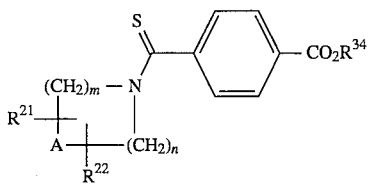

(wherein $R^{34}$ is a lower alkyl group, $R^{21}$, $R^{22}$, A, m and n are as defined above), the ester moiety of this compound is hydrolyzed by a conventional method, the resulting compound is reacted with a compound represented by the formula:

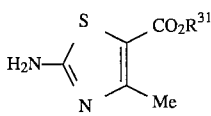

(wherein $R^{31}$ is as defined above) or a salt thereof by an ordinary method for formation of amide linkage to give a compound represented by the formula:

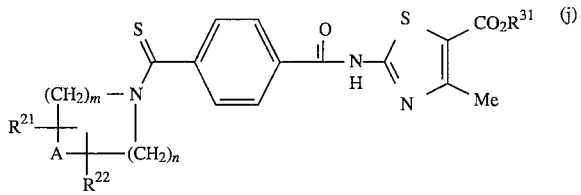

(wherein $R^{21}$, $R^{22}$, $R^{31}$, A, m and n are as defined above), which is then led to a compound represented by the formula:

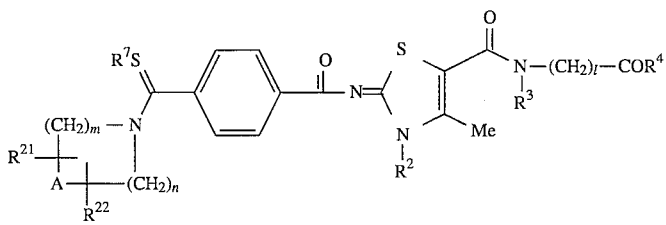

(wherein $R^2$, $R^3$, $R^4$, $R^7$, $R^{21}$, $R^{22}$, A, m, n and l are as defined above) or a salt thereof by the method similar to that described above, followed by treating with ammonia or a salt thereof to give a compound of Formula (I) wherein $R^1$ is a group of Formula (III).

Furthermore, the compound of Formula (I) can be also prepared by reacting a compound represented by the formula:

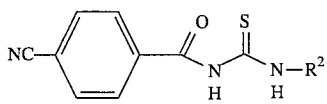

(wherein $R^2$ is as defined above) which can be prepared, for example, by a method described in Org. Synth. Coll., vol. 3, page 735, with a compound represented by the formula:

(wherein $R^{31}$ is as defined above) in the presence or absence of a base in a solvent or without solvent under heating to lead to a compound of Formula (b) wherein $R^5$ is a cyano group with subsequent procedure similar to that described above.

Examples of the base to be used in the above reactions are alkali hydroxides (e.g. sodium hydroxide or potassium hydroxide), alkali metal salts (e.g. sodium methylsulfinylmethide, sodium hydride, sodium amide or potassium tert-butoxide), amines (e.g. triethylamine, diisopropylethylamine or pyridine) and examples of amine salts to be used in the above reactions are organic acid salts (e.g. ammonium acetate).

Examples of the reaction solvent to be used are reaction-inert solvents such as alcohols (e.g. methanol, ethanol, isopropyl alcohol or tert-butyl alcohol), ethers (e.g. diethyl ether, dioxane or tetrahydrofuran), hydrocarbons (e.g. hexane, heptane, benzene, toluene or xylene), N,N-dimethylformamide, dimethyl sulfoxide, pyridine, acetic acid, methylene chloride, chloroform, acetone and water.

INDUSTRIAL UTILIZATION

The thus-obtained compounds of Formula (I) inhibit the binding of various adhesive proteins such as fibrinogen, fibronectin or von Willebrand factor against fibrinogen receptor (GpIIb/IIIa) on blood platelet, and have the inhibitory action of the aggregation and adhesion of blood platelet. Additionally, the compounds of Formula (I) inhibit the binding of the above-mentioned adhesive proteins and other adhesive proteins such as vitronectin and collagen which form intercellular matrix on various cell surfaces, and act on biotaxis and cell-intercellular interaction.

Accordingly, the compounds of the present invention can be used as preventive or therapeutic agents for ischemic diseases (e.g. thrombosis or myocardial infarction) and atherosclerosis diseases, or metastasis inhibitory agents for malignant tumors.

For the purposes, the compounds of Formula (I) are mixed with, for example, conventional fillers, binders, disintegrators, lubricants, pH moderators or solubilizers, and prepared in forms such as tablets, pills, capsules, granules, powders, solutions, emulsions, suspensions or injectional solutions by conventional pharmaceutical techniques, which can be administered orally or parenterally.

The dose for adult patients is 1 to 1000 mg in the case of oral administration, and 0.01 to 100 mg in the case of parenteral administration, which can be administered in a single dose or in several divided doses per day. This dose can be increased or decreased depending on the kind of the diseases and the age, body weight and condition of the patient.

The effect of the compounds of Formula (I) is illustrated by the following experiments.

Experiment 1

[Human Blood Platelet Fibrinogen Binding Test]

Citrated blood (the volume ratio of 3.13% sodium citrate solution and blood is 1:9) was collected from the cubital vein of a healthy human who had not received any drugs known to affect the function of blood platelet within 2 weeks prior to starting the test, and was centrifuged at 120×g at room temperature for 15 minutes to give platelet rich plasma (PRP) as a supernatant.

To the above PRP was added one fifth volume of an ACD solution (citric acid: sodium citrate: dextrose=68.7 mM: 85 mM: 11.1 mM), followed by centrifugation at 1200×g for 15 minutes. The precipitate was suspended in a Tyrode's solution (20% fetal bovine serum, 2 mM $Mg^{2+}$), followed by gel filtration using Sepharose 2B column to give a blood platelet suspension ($1\times10^9$/ml) apart from fibrinogen. The binding test was carried out by using the blood platelet suspension, a solution of the compound of Formula I as a test drug in dimethyl sulfoxide which was adjusted to the desired concentration by diluting with a physiological saline solution, adenosine diphosphate (produced by Sigma Co.; hereinafter referred to as "ADP") (final concentration: 10 μM), and $^{125}$I labelled human fibrinogen. The binding inhibition rate of the test drug was then calculated.

RGDS (produced by Sigma Co.) and 3-[3-( 4-amidinobenzoyl)benzamide]propionic acid (described in Japanese Patent Kokai 2-223543; hereinafter referred to as "control") were used as comparative drugs, and the test solutions of these drugs were prepared in the same manner as described above, and tested as described above.

The results are shown in Table 1 in which the compound numbers are as defined in the following examples.

TABLE 1

| Compound No. | $IC_{50}$ (nM) | Compound No. | $IC_{50}$ (nM) |
| --- | --- | --- | --- |
| Compound 5 | 5.1 | Compound 141 | 4.9 |
| Compound 7 | 2.7 | Compound 145 | 5.8 |
| Compound 23 | 6.3 | Compound 193 | 3.5 |
| Compound 26 | 7.0 | Compound 195 | 3.2 |
| Compound 29 | 7.9 | Compound 197 | 5.7 |
| Compound 35 | 1.0 | Compound 201 | 6.5 |
| Compound 37 | 1.3 | Compound 207 | 7.4 |
| Compound 95 | 3.3 | Compound 213 | 8.1 |
| Compound 97 | 2.5 | Compound 217 | 8.1 |
| Compound 99 | 2.7 | Compound 219 | 8.1 |
| Compound 107 | 1.6 | Compound 227 | 3.0 |
| Compound 119 | 2.9 | Control | 84.4 |
| Compound 121 | 5.1 | RGDS | 180000 |

Experiment 2

[Inhibition Test of Human In Vitro Blood Platelet Aggregation]

Citrated blood (the volume ratio of 3.13% sodium citrate solution and blood is 1:9) was collected from the cubital vein of a healthy human who had not received any drugs known to affect the function of blood platelet within 2 weeks prior to starting the test, and was centrifuged at 120×g at room temperature for 15 minutes to give platelet rich plasma (PRP) as a supernatant, then at 1500×g for 10 minutes to give platelet poor plasma (PPP). The blood platelet counts of PRP were adjusted to (50 to 60)×$10^4$/μl by diluting with PPP.

Blood platelet aggregation was determined according to the method of Born G.V.R., [Nature, vol. 194, page 927 (1962)] using ADP as an aggregation inducing substance. That is, a solution of the compound of Formula (I) as a test drug in dimethyl sulfoxide was adjust to the desired concentration with a physiological saline solution. 25 μl of the solution was added to 250 μl of PRP and incubated at 37° C. for 3 minutes, and 25 μl of ADP (final concentration: 7 μM) was added thereto. The mixture was measured for 5 minutes by using a blood platelet aggregation ability measurement apparatus (Aggricoda TM.PA-3210; made by Kyoto Daiichi Kagaku Co.) to give the maximum aggregation rate, and the concentration of the test drug to cause 50% inhibition of the maximum aggregation ($IC_{50}$) was calculated.

Results are shown in Table 2 wherein the compound numbers are as defined in the following examples, and control is as used in Experiment 1.

TABLE 2

| Compound No. | $IC_{50}$ (nM) | Compound No. | $IC_{50}$ (nM) |
| --- | --- | --- | --- |
| Compound 5 | 17 | Compound 97 | 21 |
| Compound 17 | 19 | Compound 103 | 19 |
| Compound 22 | 18 | Compound 143 | 17 |
| Compound 27 | 15 | Compound 149 | 21 |
| Compound 29 | 14 | Compound 227 | 22 |
| Compound 31 | 20 | Control | 105 |

BEST MODE FOR CARRYING OUT THE INVENTION

EXAMPLE 1

(1) A mixture of 4-cyanobenzoyl chloride (166.5 g), ethyl 2-amino-4-methylthiazole-5-carboxylate hydrochloride (224.0 g) and pyridine (2000 ml) was stirred at room temperature for 70 minutes. The precipitated crystals were collected by filtration, and washed with 3% hydrochloric acid and water to give ethyl 2-(4-cyanobenzoylamino)-4-methylthiazole-5-carboxylate (262.0 g).

m.p. 293°~295° C.

(2) The compound obtained in (1) (22.07 g) was added to a suspension of 60% sodium hydride in oil (3.08 g) in N,N-dimethylformamide (hereinafter referred to as "DMF") (300 ml) under ice-cooling, followed by stirring at room temperature for an hour. A solution of methyl iodide (4.8 ml) in DMF (50 ml) was added dropwise to the reaction mixture, followed by further stirring at room temperature for an hour. The reaction mixture was taken up in 3% hydrochloric acid, the precipitate crystals were collected by filtration, and the resulting crude crystals were recrystallized from a mixture of methylene chloride and methanol to give ethyl 2-(4-cyanobenzoylimino)- 3,4-dimethyl-3H-thiazoline-5-carboxylate (15.97 g).

m.p. 244°~245° C.

(3) 10% Aqueous sodium hydroxide solution (48 ml) was added to a mixture of the compound obtained in (2) (9.88 g), methylene chloride (250 ml) and methanol (250 ml), followed by stirring at room temperature for 17 hours. The reaction mixture was concentrated under reduced pressure, and the precipitated crystals were collected by filtration to give sodium 2-( 4-cyanobenzoylimino)-3,4-dimethyl-3H-thiazoline- 5-carboxylate (10.0 g).

$^1$H-NMR (DSMSO-$d_6$) δ(ppm):

2.66 (3H, s), 3.75 (3H, s), 7.91 (2H, d, J=8 Hz), 8.33 (2H, d, J=8 Hz)

(4) β-Alanine methyl ester hydrochloride (4.68 g), 1-hydroxybenzotriazole monohydrate (hereinafter referred to as "HOBt") (9.34 g) and 1-ethyl-3-[ 3-(dimethylamino)-propyl]carbodiimide hydrochloride (hereinafter referred to as "WSC.HCl") (6.43 g) were successively added to a suspension of the compound obtained in (3) (9.85 g) in DMF, followed by stirring at room temperature for 14 hours. The reaction mixture was taken up in water, and the precipitated crystals were collected by filtration, and recrystallized from a mixture of methylene chloride and hexane to give N-(2-methoxycarbonylethyl)-2-(4-cyanobenzoylimino)- 3,4-dimethyl-3H-thiazoline-5-carboxamide (Compound 1) (9.9 g).

m.p. 187.5°~189.5° C.

EXAMPLE 2

Hydrogen sulfide was passed through a mixture of Compound 1 (9.66 g), pyridine (500 ml) and triethylamine (8.7 ml) at room temperature with stirring for 3 hours, followed by standing for 16 hours. The solvent in the reaction mixture was evaporated under reduced pressure, and the resulting crude crystals were washed with ethyl acetate to give N-(2-methoxycarbonylethyl)-2-(4-thiocarbamoylbenzoylimino)-3,4-dimethyl-3H-thiazoline- 5-carboxamide (Compound 2) (10.56 g).

m.p. 215.5°~216.5° C.

EXAMPLE 3

Methyl iodide (28 ml) was divided into 4 portions, which were added in turn to a suspension of Compound 2 (6.31 g) in acetone (1600 ml) under reflux at intervals of 30 minutes, followed by stirring for 4 hours. The reaction mixture was concentrated under reduced pressure, and the precipitated crystals were collected by filtration to give N-(2-methoxycarbonylethyl)- 2-[4-(methylthioimidoyl)benzoylimino]-3,4-dimethyl- 3H-thiazoline-5-carboxamide hydroiodide (Compound 3) (7.69 g).

m.p. 203.5°~204° C.

EXAMPLE 4

A mixture of Compound 3 (7.31 g), ammonium acetate (4.0 g) and methanol (150 ml) was heated under reflux with stirring for 70 minutes. The reaction mixture was concentrated under reduced pressure, and the precipitated crystals were collected by filtration to give N-(2-methoxycarbonylethyl)-2-(4-amidinobenzoylimino)- 3,4-dimethyl-3H-thiazoline-5-carboxamide acetate (Compound 4) (4.96 g).

m.p. 223°~224.5° C.

EXAMPLE 5

A mixture of Compound 4 (100 mg), water (0.5 ml) and 47% aqueous HBr solution (0.5 ml) was stirred at 80° C. for 1.5 hours. The reaction mixture was ice-cooled, and the precipitated crystals were collected by filtration to give N-(2-carboxyethyl)-2-(4-amidinobenzoylimino)- 3,4-dimethyl-3H-thiazoline-5-carboxamide hydrobromide (Compound 5) (63 mg).

m.p. 272°~273.5° C.

EXAMPLE 6

Compound 3 (1.12 g) was added to a mixture of 40% methylamine-methanol (2.0 ml), methanol (15 ml) and acetic acid (1.2 ml), followed by heating under reflux with stirring for 1.5 hours. The reaction mixture was evaporated under reduced pressure, and the resulting residue was washed with methanol to give N-(2-methoxycarbonylethyl)- 2-[4-(N-methylamidino)benzoylimino]- 3,4-dimethyl-3H-thiazoline-5-carboxamide hydroiodide (Compound 6) (0.84 g).

m.p. 225°~227° C.

EXAMPLE 7

Following the procedure similar to that of Example 5 using Compound 6 (417 mg), there was obtained N-(2-carboxyethyl)-2-[4-(N-methylamidino)benzoylimino]-3,4-dimethyl-3H-thiazoline-5-carboxamide hydrobromide (Compound 7) (289 mg).

$^1$H-NMR (DMSO-d$_6$) δ(ppm):

2.50 (2H, t, J=6 Hz), 2.61 (3H, s), 3.03 (3H, d, J=5 Hz), 3.43 (2H, q, J=6 Hz), 3.85 (3H, s), 7.85 (2H, d, J=8 Hz), 8.30 (1H, t, J=6 Hz), 8.38 (2H, d, J=8 Hz), 9.02 (1H, brs), 9.55 (1H, brs), 9.88 (1H, d, J=5Hz), 12.3 (1H, brs)

EXAMPLE 8

Following the procedure similar to that of each of Examples 1 to 5, there were obtained the compounds shown in Table 3 from the corresponding starting materials.

TABLE 3

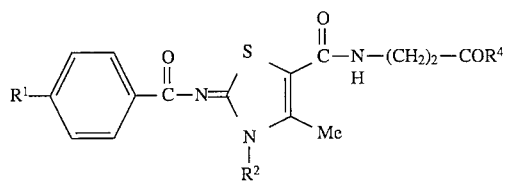

| Compound No. | R$^1$ | R$^2$ | R$^4$ | Salt | m.p. (°C.) |
|---|---|---|---|---|---|
| Compound 8 | —CN | Et | OMe | — | 153.5~155 |
| Compound 9 | —CSNH$_2$ | Et | OMe | — | 178.5~180 |
| Compound 10 | —C(NH)SMe | Et | OMe | HI | 191~192.5 |
| Compound 11 | —C(NH)NH$_2$ | Et | OMe | AcOH | 231~232.5 |
| Compound 12 | —C(NH)NH$_2$ | Et | OH | HBr | 243~245 |
| Compound 13 | —CN | PhCH$_2$ | OMe | — | 191.5~194.5 |
| Compound 14 | —CSNH$_2$ | PhCH$_2$ | OMe | — | 187~189.5 |
| Compound 15 | —C(NH)SMe | PhCH$_2$ | OMe | HI | 197~199 |
| Compound 16 | —C(NH)NH$_2$ | PhCH$_2$ | OMe | AcOH | 230.5~233 |
| Compound 17 | —C(NH)NH$_2$ | PhCH$_2$ | OH | HCl | 246.5~247.5 |
| Compound 18 | —CN | Bu | OMe | — | 155.5~157.5 |
| Compound 19 | —CSNH$_2$ | Bu | OMe | — | 177~179.5 |

TABLE 3-continued

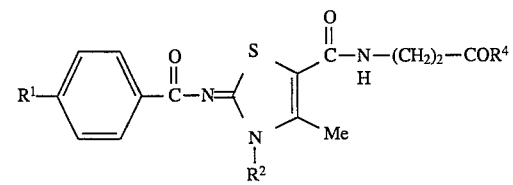

| Compound No. | R¹ | R² | R⁴ | Salt | m.p. (°C.) |
|---|---|---|---|---|---|
| Compound 20 | —C(NH)SMe | Bu | OMe | HI | 156~159 |
| Compound 21 | —C(NH)NH₂ | Bu | OMe | AcOH | 226~228 |
| Compound 22 | —C(NH)NH₂ | Bu | OH | HBr | 247~248 |
| Compound 23 | —CN | i-Pr | OMe | — | 139.5~141 |
| Compound 24 | —CSNH₂ | i-Pr | OMe | — | 172.5~174 |
| Compound 25 | —C(NH)SMe | i-Pr | OMe | HI | 193.5~196 |
| Compound 26 | —C(NH)NH₂ | i-Pr | OMe | AcOH | 222.5~224 |
| Compound 27 | —C(NH)NH₂ | i-Pr | OH | HBr | 233~235 |
| Compound 28 | —C(NH)NHCH₂Ph | Me | OMe | HI | 250~251.5 |
| Compound 29 | —C(NH)NHCH₂Ph | Me | OH | HBr | 274~275.5 |

EXAMPLE 9

Compound 3 (1.0 g) was added to a mixture of aniline (0.18 ml) and methanol (20 ml), followed by heating under reflux with stirring for 1.5 hours. The reaction mixture was evaporated under reduced pressure, and the resulting residue was washed with methanol to give N-(2-methoxycarbonylethyl)-2-[4-(N-phenylamidino)benzoylimino]- 3,4-dimethyl-3H-thiazoline-5-carboxamide hydroiodide (Compound 30 ) (0.68 g).

m.p. 211°~212° C. (decomposition)

EXAMPLE 10

Following the procedure similar to that of Example 5 using Compound 30, there was obtained N-(2-carboxyethyl)- 2-[4-(N-phenylamidino)benzoylimino]-3,4-dimethyl- 3H-thiazoline-5-carboxamide hydrobromide (Compound 31).

m.p. 202°~204° C.

EXAMPLE 11

A mixture of Compound 4 (0.463 g), methanesulfonic acid (0.1 ml) and ethanol (20 ml) was heated under reflux for 6 hours. The reaction mixture was allowed to stand for cooling, and the precipitated crystals were collected by filtration to give N-( 2-ethoxycarbonylethyl)-2-(4-amidinobenzoylimino)- 3,4-dimethyl-3H-thiazoline-5-carboxamide methanesulfonate (Compound 32) (0.408 g).

m.p. 252°~253° C.

EXAMPLE 12

A mixture of Compound 4 (0.463 g), methanesulfonic acid (0.1 ml) and 2-propanol (20 ml) was heated under reflux for 50 hours. The reaction mixture was allowed to stand for cooling, and the precipitated crystals were collected by filtration to give N-( 2-isopropoxycarbonylethyl)-2-(4-amidinobenzoylimino)- 3,4-dimethyl-3H-thiazoline-5-carboxamide methanesulfonate (Compound 33) (0.42 g).

m.p. 253°~253.5° C.

EXAMPLE 13

A mixture of Compound 3 (1.0 g), N-methylbenzylamine (1.15 ml), acetic acid (1.21 ml) and methanol (25 ml) was heated under reflux with stirring for 90 minutes. Water was added to the reaction mixture, and the precipitated crystals were collected by filtration to give N-(2-methoxycarbonylethyl)-2-[ 4-(N-methyl-N-benzylamidino)benzoylimino]-3, 4-dimethyl-3H-thiazoline-5-carboxamide hydroiodide (Compound 34) (0.36 g).

m.p. 205°~206° C.

EXAMPLE 14

A mixture of Compound 34 (0.3 g), water (0.9 ml) and 47% aqueous hydrobromic acid solution (0.9 ml) was stirred at 80° C. for 1.5 hours. The reaction mixture was ice-cooled, and the precipitated crystals were collected by filtration to give N-(2-carboxyethyl)-2-[ 4-(N-methyl-N-benzylamidino)benzoylimino]-3,4-dimethyl-3H-thiazoline- 5-carboxamide hydrobromide (Compound 35) (0.202 g).

m.p. 259.5°~260° C.

EXAMPLE 15

A mixture of Compound 3 (1.0 g), dimethylamine acetate (1.26 g) and methanol (25 ml) was heated under reflux with stirring for 90 minutes. The reaction mixture was evaporated under reduced pressure, and the precipitated crystals were washed with methanol and acetone to give N-(2-methoxycarbonylethyl)-2-[ 4-(N,N-dimethylamidino)benzoylimino] -3,4-dimethyl-3H-thiazoline- 5-carboxamide hydroiodide (Compound 36) (0.42 g).

m.p. 254°~256° C.

EXAMPLE 16

Following the procedure similar to that of Example 14 using Compound 36, there was obtained N-( 2-carboxyethyl)-2-[4-(N,N-dimethylamidino)benzoylimino]- 3,4-dimethyl-3H-thiazoline-5-carboxamide hydrobromide (Compound 37).

m.p. 275°~275.5° C.

EXAMPLE 17

Methyl chlorocarbonate (0.18 ml) was added dropwise to a mixture of Compound 4 (1.0 g), triethylamine (0.66 ml), water (10 ml) and tetrahydrofuran (10 ml), followed by stirring at room temperature for 2 hours. The reaction mixture was concentrated under reduced pressure, and the precipitated crystals were collected by filtration to give N-(2-methoxycarbonylethyl)- 2-[4-(N-methoxycarbonylamidino)benzoylimino]- 3,4-dimethyl-3H-thiazoline-5-carboxamide (Compound 38) (0.722 g).

m.p. 280°~281° C.

EXAMPLE 18

Triethylamine (0.9 ml) was added dropwise to a mixture of Compound 4 (1.48 g), di-tert-butyldicarbonate (1.05 g), water (30 ml) and tetrahydrofuran (30 ml) under ice-cooling, followed by stirring at room temperature for 2 hours. The reaction mixture was concentrated under reduced pressure, and the precipitated crystals were collected by filtration to give N-(2-methoxycarbonylethyl)- 2-[4-(N-tert-butoxycarbonylamidino)benzoylimino]-3,4-dimethyl-3H-thiazoline-5-carboxamide (Compound 39) (1.47 g).

m.p. 202°~203° C.

EXAMPLE 19

A mixture of Compound 39 (0.906 g), 10% sodium hydroxide solution (0.88 ml) and methanol (10 ml) was stirred at room temperature for an hour. The reaction mixture was concentrated under reduced pressure, dioxane was added thereto, and the precipitated crystals were collected by filtration to give N-(2-carboxyethyl)-2-[ 4-(N-tert-butoxycarbonylamidino)benzoylimino]- 3,4-dimethyl-3H-thiazoline-5-carboxamide sodium salt (Compound 40 ) (0.58 g ).

$^1$H-NMR (DMSO-$d_6$) δ(ppm):

1.45 (9H, s), 2.09 (2H, t, J=6 Hz), 2.62 (3H, s), 3.43 (2H, q, J=6 Hz), 3.83 (3H, s), 8.03 (2H, d, J=8 Hz), 8.26 (2H, d, J=8 Hz), 9.00 (1H, t, J=6 Hz), 9.12 (2H, brs)

EXAMPLE 20

β-Alanine benzyl ester p-toluenesulfonate (8.68 g), HOBt (6.88 g) and WSC.HCl (4.73 g) were successively added to a suspension of the compound obtained in Example 1(3) (7.26 g) in DMF (150 ml) with stirring, followed by stirring at room temperature for 14 hours. The reaction mixture was taken up in water, and the precipitated crystals were collected by filtration and recrystallized from a mixture of methylene chloride and hexane to give N-(2-benzyloxycarbonylethyl)- 2-(4-cyanobenzoylimino)-3,4-dimethyl-3H-thiazoline- 5-carboxamide (Compound 41) (9.37 g).

$^1$H-NMR (DMSO-$d_6$) δ(ppm):

2.68 (2H, t, J=7 Hz), 2.70 (3H, s), 3.69 (2H, q, J=7 Hz), 3.85 (3H, s), 5.16 (2H, s), 6.40 (1H, t, J=7 Hz), 7.3~7.4 (5H, m), 7.75 (2H, m), 8.42 (2H, m)

EXAMPLE 21

Following the reaction procedure similar to that of each of Examples 2 to 4 using Compound 41, there were obtained the following compounds.

N-(2-Benzyloxycarbonylethyl)-2-(4-thiocarbamoylbenzoylimino)- 3,4-dimethyl-3H-thiazoline-5-carboxamide (Compound 42).

m.p. 179°~180.5° C.

N-(2-Benzyloxycarbonylethyl)-2-[ 4-(methylthioimidoyl)benzoylimino]-3,4-dimethyl-3H-thiazoline- 5-carboxamide hydroiodide (Compound 43).

m.p. 174.5°~175° C.

N-(2-Benzyloxycarbonylethyl)-2-(4-amidinobenzoylimino)- 3,4-dimethyl-3H-thiazoline-5-carboxamide acetate (Compound 44).

m.p. 221°~221.5° C.

EXAMPLE 22

A mixture of Compound 18 (5.0 g), 10% sodium hydroxide solution (21 ml), methylene chloride (50 ml) and methanol (100 ml) was stirred at room temperature for 30 minutes. The reaction mixture was concentrated under reduced pressure and poured into 3% aqueous hydrochloric acid solution, and the precipitated crystals were collected by filtration to give N-( 2-carboxyethyl)-2-(4-cyanobenzoylimino)-3-butyl-4-methyl- 3H-thiazoline-5-carboxamide (Compound 45) (4.34 g).

m.p. 201°~206° C.

EXAMPLE 23

WSC.HCl (2.13 g) was added to a mixture of Compound 45 (4.14 g), 2-hydroxymethylpyridine (1.18 g), 4-dimethylaminopyridine (0.24 g), HOBt (3.06 g) and DMF (50 ml), followed by stirring at room temperature for 16 hours. The reaction mixture was poured into water and extracted with ethyl acetate. The ethyl acetate layer was washed with a saturated aqueous sodium chloride solution, dried over anhydrous magnesium sulfate, and evaporated under reduced pressure. The residue was chromatographed on silica gel column with ethyl acetate to give N-[2-(pyridin-2-ylmethoxycarbonyl)ethyl]-2-( 4-cyanobenzoylimino)-3-butyl-4-methyl-3H-thiazoline- 5-carboxamide (Compound 46) (2.98 g).

m.p. 127°~129° C.

EXAMPLE 24

Following the reaction procedure similar to that of each of Examples 2 to 4 using Compound 46, there were obtained the following compounds.

N-[2-(Pyridin-2-ylmethoxycarbonyl)ethyl]-2-( 4-thiocarbamoylbenzoylimino)-3-butyl-4-methyl-3H-thiazoline- 5-carboxamide (Compound 47).

m.p. 134°~135° C.

N-[2-(Pyridin-2-ylmethoxycarbonyl)ethyl]-2-[ 4-(methylthioimidoyl)benzoylimino]-3-butyl-4-methyl- 3H-thiazoline-5-carboxamide hydroiodide-acetone solvate (Compound 48).

m.p. 150.5°~152° C.

N-[2-(Pyridin-2-ylmethoxycarbonyl)ethyl]-2-( 4-amidinobenzoylimino)-3-butyl-4-methyl-3H-thiazoline- 5-carboxamide acetate (Compound 49).

m.p. 202°~204° C.

EXAMPLE 25

A mixture of Compound 4 (371 mg), 2-methoxyethanol (5 ml) and methanesulfonic acid (0.1 ml) was stirred at 50° C. for an hour and then at room temperature for 1.5 hours. The precipitated crystals were collected by filtration to give N-(2-methoxyethoxycarbonylethyl)- 2-(4-amidinobenzoylimino)-3,4-dimethyl- 3H-thiazoline-5-carboxamide methanesulfonate (Compound 50) (166 mg).

m.p. 213°~215° C.

EXAMPLE 26

Following the procedure similar to that of Example 25 using Compound 4 and 2-(2-methoxyethoxy)ethanol, there was obtained N-[2-(2-methoxyethoxy)ethoxycarbonylethyl]- 2-(4-amidinobenzoylimino)-3,4-dimethyl- 3H-thiazoline-5-carboxamide methanesulfonate (Compound 51).

m.p. 183.5°~186° C.

EXAMPLE 27

10% Aqueous sodium hydroxide solution (3.12 ml) was added to a mixture of Compound 1 (3.00 g), methylene chloride (30 ml), dioxane (30 ml) and water (30 ml), followed by stirring at 80° C. for 2.5 hours. The reaction mixture was concentrated under reduced pressure. To a suspension of the resulting residue in DMF (100 ml) was added dropwise a solution of pivaloyloxymethyl iodide (3.63 g) in DMF (20 ml), followed by stirring at room temperature for 16 hours. The reaction mixture was taken up in water, and the precipitated crystals were collected by filtration and washed with methylene chloride to give N-( 2-pivaloyloxymethoxycarbonylethyl)-2-(4-cyanobenzoylimino)- 3,4-dimethyl-3H-thiazoline-5-carboxamide (Compound 52) (658 mg).

m.p. 113°~115° C.

EXAMPLE 28

Following the reaction procedure similar to that of each of Examples 2 and 3 using Compound 52, there were obtained the following compounds.

N-(2-Pivaloyloxymethoxycarbonylethyl)-2-( 4-thiocarbamoylbenzoylimino)-3,4-dimethyl-3H-thiazoline- 5-carboxamide (Compound 53).

m.p. 194.5°~198° C.

N-(2-Pivaloyloxymethoxycarbonylethyl)-2-[ 4-(methylthioimidoyl)benzoylimino]-3,4-dimethyl-3H-thiazoline-5-carboxamide hydroiodide (Compound 54).

m.p. 173°~173.5° C.

EXAMPLE 29

10% Aqueous sodium hydroxide solution (20 ml) was added to a mixture of Compound 1 (5.00 g), methylene chloride (20 ml) and methanol (20 ml), followed by stirring at room temperature for 2 hours. After evaporation of the solvent of the reaction mixture, 3% hydrochloric acid was added, and the precipitated crystals were collected by filtration to give N-( 2-carboxyethyl)-2-(4-cyanobenzoylimino)-3,4-dimethyl- 3H-thiazoline-5-carboxamide (Compound 55) (4.65 g).

m.p. 247°~247.5° C.

EXAMPLE 30

N,N-Dimethylethanolamine (0.59 ml), WSC.HCl (1.13 g) and 4-dimethylaminopyridine (0.12 g) were successively added to a suspension of Compound 55 (2.00 g) in DMF with stirring, followed by stirring at room temperature for 14 hours. The reaction mixture was taken up in water and extracted with ethyl acetate. The ethyl acetate layer was washed with a saturated aqueous sodium chloride solution, dried over anhydrous magnesium sulfate and concentrated under reduced pressure. The residue was chromatographed on silica gel column with methanol-methylene chloride to give N-[ 2-(N,N-dimethylaminoethoxy)carbonylethyl]-2-(4-cyanobenzoylimino)- 3,4-dimethyl-3H-thiazoline-5-carboxamide (Compound 56) (1.01 g).

m.p. 131°~133.5° C.

EXAMPLE 31

Following the reaction procedure similar to that of each of Examples 30 and 2 using Compound 55 (2.0 g) and 4-(2-hydroxyethyl)morpholine (0.72 ml), there were obtained the following compounds.

N-[2-(2-Morpholinoethoxycarbonyl)ethyl]-2-( 4-cyanobenzoylimino)-3,4-dimethyl-3H-thiazoline- 5-carboxamide (Compound 57).

m.p. 107°~109° C.

N-[2-(2-Morpholinoethoxycarbonyl)ethyl]-2-( 4-thiocarbamoylbenzoylimino)-3,4-dimethyl-3H-thiazoline- 5-carboxamide (Compound 58).

$^1$H-NMR (DMSO-$d_6$) δ(ppm):

2.40 (4H, t, J=6 Hz), 2.54 (2H, t, J=6 Hz), 2.57 (2H, t, J=6 Hz), 2.60 (3H, s), 3.45 (2H, q, J=6 Hz), 3.54 (2H, t, J=6 Hz), 3.66 (2H, t, J=6 Hz), 3.83 (3H, s), 4.14 (2H, t, J=6 Hz), 7.95 (2H, d, J=8 Hz), 8.22 (2H, d, J=8 Hz), 8.30 (1H, t, J=6 Hz), 9.61 (1H, brs), 9.99 (1H, brs).

EXAMPLE 32

Compound 1 (3.09 g) was added to a suspension of 60% sodium hydride in oil (0.384 g) in DMF (30 ml) under ice-cooling, followed by stirring at room temperature for an hour. Methyl iodide (0.60 ml) was added to the reaction mixture, followed by further stirring at room temperature for 40 minutes. The reaction mixture was taken up in water, the precipitated crystals were collected by filtration, and the resulting crude crystals were chromatographed on silica gel column with ethyl acetate and recrystallized from a mixture of methylene chloride and hexane to give N-methyl-N-( 2-methoxycarbonylethyl)-2-(4-cyanobenzoylimino)- 3,4-dimethyl-3H-thiazoline-5-carboxamide (Compound 59) (15.97 g).

m.p. 195.5°~197.5° C.

EXAMPLE 33

Following the reaction procedure similar to that of each of Examples 2 to 4 using Compound 59, there were obtained the following compounds.

N-Methyl-N-(2-methoxycarbonylethyl)-2-( 4-thiocarbamoylbenzoylimino)-3,4-dimethyl-3H-thiazoline- 5-carboxamide (Compound 60).

m.p. 219°~220° C.

N-Methyl-N-(2-methoxycarbonylethyl)-2-[ 4(methylthioimidoylbenzoylimino]-3,4-dimethyl- 3H-thiazoline-5-carboxamide hydroiodide (Compound 61).

$^1$H-NMR (DMSO-$d_6$) δ(ppm):

2.33 (3H, s), 2.66 (3H, t, J=6 Hz), 2.84 (3H, s), 2.99 (3H, s), 3.60 (3H, s), 3.66 (2H, t, J=6 Hz), 3.83 (3H, s), 7.97 (2H, d, J=8 Hz), 8.42 (2H, d, J=8 Hz).

N-Methyl-N-(2-methoxycarbonylethyl)-2-(4-amidinobenzoylimino)- 3,4-dimethyl-3H-thiazoline-5-carboxamide acetate (Compound 62).

m.p. 202°~203° C.

EXAMPLE 34

A mixture of Compound 62 (0.5 g), water (2.0 ml) and 47% aqueous hydrobromic acid solution (1.5 ml) was stirred at 80° C. for an hour. The reaction mixture was ice-cooled, and the precipitated crystals were collected by filtration to give N-methyl-N-( 2-carboxyethyl)-2-(4-amidinobenzoylimino)-3,4-dimethyl- 3H-thiazoline-5-carboxamide hydrobromide (Compound 63) (0.14 g).

m.p. 215°~223° C.

EXAMPLE 35

N,N-dimethyl-2-chloroacetamide (0.19 ml) was added to a mixture of Compound 40 (0.87 g), DMF (15 ml) and sodium iodide (0.28 g), followed by stirring at room temperature for 5 hours. The reaction mixture was taken up in water and the precipitated crystals were collected by filtration to give N-[2-(N,N-dimethylcarbamoylmethoxycarbonyl)ethyl]-2-[4-(N-tert-butoxycarbonylamidino)benzoylimino]-3,4-dimethyl-3H-thiazoline-5-carboxamide (Compound 64) (0.83 g).

m.p. 167°~169° C.

EXAMPLE 36

Trifluoroacetic acid (7 ml) was added to a solution of Compound 64 (0.75 g) in methylene chloride (5 ml), followed by stirring at room temperature for 2 hours. Water was added to the reaction mixture, and the precipitated crystals were collected by filtration to give N-[2-(N,N-dimethylcarbamoylmethoxycarbonyl)ethyl]-2-(4-amidinobenzoylimino)-3,4-dimethyl-3H-thiazoline- 5-carboxamide trifluoroacetate (Compound 65) (0.754 g).

m.p. 218°~219° C.

EXAMPLE 37

Following the reaction procedure similar to that of each of Examples 35 and 36 using Compound 40, there were obtained the following compounds.

N-[2-(N,N-Diethylcarbamoylmethoxycarbonyl)ethyl]-2-[4-(N-tert-butoxycaronylamidino)benzoylimino]-3,4-dimethyl-3H-thiazoline-5-carboxamide (Compound 66).

m.p. 154°~156° C.

N-[2-(N,N-Diethylcarbamoylmethoxycarbonyl)ethyl]-2-(4-amidinobenzoylimino)-3,4-dimethyl- 3H-thiazoline-5-carboxamide trifluoroacetate (Compound 67).

m.p. 206.5°~207.5° C.

EXAMPLE 38

Glycine methyl ester hydrochloride (1.07 g), HOBt (2.37 g) and WSC. HCl (1.63 g) were successively added to a suspension of the compound obtained in Example 1(3) (2.5 g) in DMF (45 ml) with stirring, followed by stirring at room temperature for 14 hours. The reaction mixture was taken up in water, and the precipitated crystals were collected by filtration and recrystallized from a mixture of methylene chloride and hexane to give N-(methoxycarbonylmethyl)-2-( 4-cyanobenzoylimino)-3,4-dimethyl-3H-thiazoline-5-carboxamide (Compound 68) (2.25 g).

m.p. 238°~238.5° C.

EXAMPLE 39

Following the reaction procedure similar to that of each of Examples 2 to 4 using Compound 68, there were obtained the following compounds.

N-(Methoxycarbonylmethyl)-2-(4-thiocarbamoylbenzoylimino)- 3,4-dimethyl-3H-thiazoline-5-carboxamide (Compound 69).

m.p. 235°~235.5° C.

N-(Methoxycarbonylmethyl)-2-[4-(methylthioimidoyl)benzoylimino]-3,4-dimethyl-3H-thiazoline-5-carboxamide hydroiodide (Compound 70).

m.p. 216.5°~217° C.

N (Methoxycarbonylmethyl)-2-(4-amidinobenzoylimino)-3,4-dimethyl-3H-thiazoline-5-carboxamide acetate (Compound 71).

m.p. 236.5°~237° C.

EXAMPLE 40

A mixture of Compound 71 (0.15 g), 10% aqueous sodium hydroxide solution (0.3 ml) and methanol (5 ml) was stirred at 50° C. for 3 hours. 3% Hydrochloric acid was added to the reaction mixture, and the precipitated crystals were collected by filtration to give N-(carboxymethyl)-2-(4-amidinobenzoylimino)-3,4-dimethyl- 3H-thiazoline-5-carboxamide hydrochloride (Compound 72) (0.072 g).

m.p. 289°~289.5° C.

EXAMPLE 41

Methyl 4-aminobutyrate hydrochloride (1.57 g), HOBt (2.84 g) and WSC.HCl (1.96 g) were successively added to a suspension of the compound obtained in Example 1(3) (3.0 g) in DMF (55 ml) with stirring, followed by stirring at room temperature for 14 hours. The reaction mixture was taken up in water, and the precipitated crystals were collected by filtration and recrystallized from a mixture of methylene chloride and hexane to give N-(3-methoxycarbonylpropyl)-2-( 4-cyanobenzoylimino)-3,4-dimethyl-3H-thiazoline-5-carboxamide (Compound 73) (3.27 g).

m.p. 182°~184.5° C.

EXAMPLE 42

Following the reaction procedure similar to that of each of Examples 2 to 5 using Compound 73, there were obtained the following compounds.

N-(3-Methoxycarbonylpropyl)-2-( 4-thiocarbamoylbenzoylimino)-3,4-dimethyl-3H-thiazoline- 5-carboxamide (Compound 74).

$^1$ H-NMR (DMSO-$d_6$) δ(ppm):

1.76 (2H, m), 2.36 (2H, t, J=7 Hz), 2.60 (3H, s), 3.23 (2H, q, J=7 Hz), 3.60 (3H, s), 3.82 (3H, s), 7.95 (2H, d, J=8 Hz), 8.22 (2H, d, J=8 Hz), 9.62 (1H, s), 9.98 (1H, s)

N-(3-Methoxycarbonylpropyl)-2-[ 4-(methylthioimidoyl)benzoylimino]-3,4-dimethyl-3H-thiazoline- 5-carboxamide hydroiodide (Compound 75).

m.p. 188°~189° C.

N-(3-carboxypropyl)-2-(4-amidinobenzoylimino)-3,4-dimethyl-3H-thiazoline-5-carboxamide hydrobromide (Compound 76).

m.p. 234.5°~237° C.

EXAMPLE 43

Following the procedure similar to that of Example 41 using sodium 2-(4-cyanobenzoylimino)- 3-isopropyl-4-methyl-3H-thiazoline-5-carboxylate which was obtained by carrying out the reactions similar to those of Example 1(1) to 1(3) using isopropyl iodide instead of methyl iodide, there was obtained N-(3-methoxycarbonylpropyl)- 2-(4-cyanobenzoylimino)-3-isopropyl- 4-methyl-3H-thiazoline-5-carboxamide (Compound 77).

m.p. 138°~139° C.

EXAMPLE 44

Following the procedure similar to that of Example 2 using Compound 77, there was obtained N-( 3-methoxycarbonylpropyl)-2-(4-thiocarbamoylbenzoylimino)-3-isopropyl-4-methyl-3H-thiazoline-5-carboxamide (Compound 78).

m.p. 106°~107.5° C.

EXAMPLE 45

Following the reaction procedure similar to that of each of Examples 1(4) and 2 using sodium 2-( 4-cyanobenzoylimino)-3-isopropyl-4-methyl-3H-thiazoline- 5-carboxylate and the corresponding materials, there were obtained the following compounds.

N-(5-Methoxycarbonylpentyl)-2-( 4-cyanobenzoylimino)-3-isopropyl-4-methyl-3H-thiazoline- 5-carboxamide (Compound 79).

m.p. 158.5°~160.5° C.

N-(5-Methoxycarbonylpentyl)-2-( 4-thiocarbamoylbenzoylimino)-3-isopropyl-4-methyl- 3H-thiazoline-5-carboxamide (Compound 80).

m.p. 119.5°~120.5° C.

EXAMPLE 46

6N Aqueous sodium hydroxide solution (0.12 ml) was added to a mixture of Compound 23 (0.2 g), methylene chloride (6 ml) and methanol (6 ml), followed by stirring at room temperature for 3 days. 30% Aqueous hydrogen peroxide solution (0.23 ml) was added, and the mixture was stirred at room temperature for 4 hours. 5% Aqueous sodium thiosulfate solution was added to the reaction mixture, the solvent was evaporated, and 3% hydrochloric acid was added. The precipitated crystals were collected by filtration to give N-(2-carboxyethyl)-2-(4-carbamoylbenzoylimino)-3-isopropyl-4-methyl- 3H-thiazoline-5-carboxamide (Compound 81).

m.p. 241°~243° C.

EXAMPLE 47

2M Ammonia/methanol (10 ml) was added to a solution of Compound 23 (0.2 g) in methylene chloride (2 ml), followed by stirring at room temperature for 3 days. The reaction mixture was evaporated. To a solution of the resulting residue in methanol (10 ml) were added 6N aqueous sodium hydroxide solution (0.25 ml) and 30% aqueous hydrogen peroxide solution (0.23 ml), followed by stirring at room temperature for 2.5 hours. 3% Hydrochloric acid was added to the reaction mixture, the solvent was evaporated, and crystallization from a mixture of acetone and methylene chloride gave N-( 2-carbamoylethyl)-2-(4-carbamoylbenzoylimino)-3-isopropyl-4-methyl-3H-thiazoline-5-carboxamide (Compound 82).

m.p. 204°~208° C.

EXAMPLE 48

(1) Ethyl 2-(4-cyanobenzoylamino)-4-methylthiazole-5-carboxylate (5.0 g) was added to a suspension of 60% sodium hydride in oil (0.76 g) in DMF (60 ml) under ice-cooling, followed by stirring at room temperature for an hour. A solution of 1-chloromethylnaphthalene (3.37 g) in DMF (5 ml) was added dropwise to the reaction mixture, followed by further stirring at room temperature for 14 hours. The reaction mixture was taken up in 3% hydrochloric acid, the precipitated crystals were collected by filtration and chromatographed on silica gel column with methylene chloride, and the resulting crude crystals were recrystallized from a mixture of methylene chloride and methanol to give ethyl 2-(4-cyanobenzoylimino)-3-(1-naphthylmethyl)-4-methyl-3H-thiazoline-5-carboxylate (1.86 g).

m.p. 229°~229.5° C.

(2) Following the reaction procedures similar to those of Example 1(3) and 1(4) using ethyl 2-( 4-cyanobenzoylimino)-3-(1-naphthylmethyl)-4-methyl- 3H-thiazoline-5-carboxylate, there was obtained ethyl N-( 2-methoxycarbonylethyl)-2-(4-cyanobenzoylimino)-3-( 1-naphthylmethyl)-4-methyl-3H-thiazoline-5-carboxamide (Compound 83).

m.p. 230°~231° C.

EXAMPLE 49

Following the reaction procedure similar to that of each of Examples 2 and 3 using Compound 83, there were obtained the following compounds.

N-(2-Methoxycarbonylethyl)-2-(4-thiocarbamoylbenzoylimino)- 3-(1-naphthylmethyl)-4-methyl-3H-thiazoline-5-carboxamide (Compound 84).

m.p. 217°~218° C.

N-(2-Methoxycarbonylethyl)-2-[4-(methylthioimidoyl)benzoylimino-]-3-(1-naphthylmethyl)-4-methyl-3H-thiazoline- 5-carboxamide hydroiodide (Compound 85).

m.p. 166°~169° C.

EXAMPLE 50

(1) Ethyl 2-(4-cyanobenzoylamino)-4-methylthiazole-5-carboxylate (5.0 g) was added to a suspension of 60% sodium hydride in oil (0.76 g) in DMF (60 ml) under ice-cooling, followed by stirring at room temperature for an hour. 1-Iodohexane (8.46 ml) was added dropwise to the reaction mixture, followed by further stirring at room temperature for 14 hours. The reaction mixture was taken up in 3% hydrochloric acid and extracted with methylene chloride. The methylene chloride layer was evaporated under reduced pressure and crystallized from hexane to give ethyl 2-( 4-cyanobenzoylimino)-3-hexyl-4-methyl-3H-thiazoline-5-carboxylate (3.86 g).

m.p. 125°~126° C.

(2) Following the reaction procedures similar to those of Example 1(3) and 1(4) using ethyl 2-( 4-cyanobenzoylimino)-3-hexyl-4-methyl-3H-thiazoline- 5-carboxylate, there was obtained N-(2-methoxycarbonylethyl)- 2-(4-cyanobenzoylimino)-3-hexyl-4-methyl-3H-thiazoline- 5-carboxamide (Compound 86).

m.p. 100°~104° C.

EXAMPLE 51

Following the reaction procedure similar to that of each of Examples 2 to 5 using Compound 86, there were obtained the following compounds.

N-(2-Methoxycarbonylethyl)-2-(4-thiocarbamoylbenzoylimino)- 3-hexyl-4-methyl-3H-thiazoline-5-carboxamide (Compound 87).

m.p. 176.5°~178° C.

N-(2-Methoxycarbonylethyl)-2-[4-(methylthioimidoyl)benzoylimino]-3-hexyl-4-methyl-3H-thiazoline- 5-carboxamide hydroiodide (Compound 88).

m.p. 192.5°~194° C.

N-(2-Methoxycarbonylethyl)-2-(4-amidinobenzoylimino)- 3-hexyl-4-methyl-3H-thiazoline-5-carboxamide acetate (Compound 89).

m.p. 194.5°~195° C.

N-(2-Carboxyethyl)-2-(4-amidinobenzoylimino)-3-hexyl-4-methyl-3H-thiazoline-5-carboxamide hydrobromide (Compound 90).

m.p. 186.5°~190° C.

EXAMPLE 52

(1) A mixture of methyl 4-formylbenzoate (11.5 g), sulfur (2.28 g) and morpholine (140 ml) was heated under reflux for 20 minutes. The reaction mixture was allowed to stand for cooling, the insolubles were filtered off, and the filtrate was poured into 3% hydrochloric acid and extracted with ethyl acetate. The ethyl acetate layer was washed with 5% aqueous sodium bicarbonate solution and a saturated aqueous sodium chloride solution, dried over anhydrous magnesium sulfate, evaporated under reduced pressure, and recrystallized from an aqueous methanol to give methyl 4-(morpholinothiocarbonyl)benzoate (15.7 g).

m.p. 123.5°~125° C.

(2) A mixture of the compound obtained in (1)(6.1 g), 10% sodium hydroxide solution (18 ml) and methanol (100 ml) was stirred at room temperature for 2 hours. The reaction mixture was concentrated under reduced pressure and poured into 3% hydrochloric acid, and the precipitated crystals were collected by filtration to give 4-(morpholinothiocarbonyl)benzoic acid (5.29 g).

m.p. 227°~230° C.

(3) Triethylamine (3.1 ml) was added dropwise to a mixture of the compound obtained in (2) (5.0 g), ethyl 2-amino-4-methylthiazole-5-carboxylate hydrochloride (4.43 g), HOBt (6.09 g), WSC.HCl (4.22 g) and DMF (100 ml), followed by stirring at room temperature for 14 hours and then at 60° C. for 3 hours. The reaction mixture was taken up in water, and the precipitated crystals were collected by filtration and recrystallized from a mixture of ethyl acetate and hexane to give ethyl 2-[4-(morpholinothiocarbonyl)benzoylamino]-4-methylthiazole- 5-carboxylate-DMF solvate (8.34 g).

m.p. 265° C. (decomposition)

(4) Following the reaction procedures similar to those of Example 1(2) to 1(4) using the compound obtained in (3), there were obtained the following compounds.

Ethyl 2-[4-(morpholinothiocarbonyl)benzoylimino]-3,4-dimethyl-3H-thiazoline-5-carboxylate.

m.p. 203°~206° C.

N-(2-Methoxycarbonylethyl)-2-[4-(morpholinothiocarbonyl)benzoylimino]-3,4-dimethyl-3H-thiazoline-5-carboxamide (Compound 91).

m.p. 227.5°~231° C.

EXAMPLE 53

(1) Following the reaction procedure similar to that of Example 3 using Compound 91, there was obtained α-methylthio-4-{[5-[2-(methoxycarbonyl)ethylaminocarbonyl]-3,4-dimethyl-3H-thiazoline-2-dene]aminocarbonyl} benzylidene morpholinium iodide.

m.p. 202.5°~205° C.

(2) A mixture of α-methylthio-4-{[5-[ 2-(methoxycarbonyl)ethylaminocarbonyl]-3,4-dimethyl-3H-thiazoline-2-dene]aminocarbonyl}benzylidene morpholinium iodide (3.02 g), 1,2-diaminoethane (0.3 g) and methanol (100 ml) was heated under reflux with stirring for 2 hours. The reaction mixture was concentrated under reduced pressure, and the precipitated crystals were collected by filtration to give N-(2-methoxycarbonylethyl)-2-[ 4-(imidazolin-2-yl)benzoylimino]-3,4-dimethyl-3H-thiazoline- 5-carboxamide acetate (Compound 92).

$^1$H-NMR (DMSO-d$_6$) δ(ppm):

2.58 (2H, t, J=6 Hz), 2.60 (3H, s), 3.46 (2H, q, J=6 Hz), 3.61 (4H, m), 3.85 (6H, s), 7.98 (2H, m), 8.32 (1H, t, J=6 Hz), 8.34 (2H, m)

EXAMPLE 54

Following the reaction procedure similar to that of Example 40 using Compound 92, there was obtained N-(2-carboxyethyl)-2-[4-(imidazolin-2-yl)benzoylimino]-3,4-dimethyl-3H-thiazoline-5-carboxamide hydrochloride (Compound 93).

$^1$H-NMR (DMSO-d$_6$) δ(ppm):

2.27 (3H, s), 2.63 (2H, t, J=6 Hz), 3.50 (2H, t, J=6 Hz), 3.58 (3H, s), 4.08 (4H, brs), 7.69 (2H, m), 8.06 (2H, m)

EXAMPLE 55

Following the reaction procedure similar to that of each of Examples 5, 9, 13, 15 and 40 using Compound 3 (or Compound 25), there were obtained the following compounds shown in Tables 4 and 5 (Compounds 94 to 137).

TABLE 4

[Structure: R¹–C₆H₄–C(=O)–N=C(S–)(N(Me)₂)... with C=C(Me)–C(=O)–NH–(CH₂)₂–COR⁴]

| Compound No. | R¹ | R⁴ | Salt | m.p. (°C.) |
|---|---|---|---|---|
| Compound 94 | –C(NH)NH–C₆H₄–OMe | OMe | HI | 223–226 |
| Compound 95 | –C(NH)NH–C₆H₄–OMe | OH | HBr | 260–260.5 |
| Compound 96 | –C(NH)NH–C₆H₄–Me | OMe | HI | 202–204 |
| Compound 97 | –C(NH)NH–C₆H₄–Me | OH | HBr | 253.5–255.5 |
| Compound 98 | –C(NH)NH–C₆H₄–Cl | OMe | HI | 222–225.5 |
| Compound 99 | –C(NH)NH–C₆H₄–Cl | OH | HBr | 228.5–232 |
| Compound 100 | –C(NH)NH–C₆H₄–F | OMe | HI | 233–235 |
| Compound 101 | –C(NH)NH–C₆H₄–F | OH | HBr | 181–183 |
| Compound 102 | –C(NH)NH–CH₂–C₆H₄–OMe | OMe | HI | 207–209.5 |
| Compound 103 | –C(NH)NH–CH₂–C₆H₄–OMe | OH | HBr | 247.5–249.5 |
| Compound 104 | –C(NH)NH–CH₂–C₆H₄(o-OMe) | OMe | HI | 183–185.5 |
| Compound 105 | –C(NH)NH–CH₂–C₆H₄(o-OMe) | OH | HBr | 239.5–240 |

TABLE 4-continued $$R^1-\underset{O}{\underset{\|}{C}}-N=\underset{\underset{Me}{N}}{C}-\underset{Me}{\overset{S}{\underset{\|}{C}}}=\underset{Me}{C}-\underset{H}{\overset{O}{\underset{\|}{C}}}-\underset{H}{N}-(CH_2)_2-COR^4$$

| Compound No. | R¹ | R⁴ | Salt | m.p. (°C.) |
|---|---|---|---|---|
| Compound 106 | —C(NH)NH—CH₂—C₆H₄—F | OMe | HI | 234~237 |
| Compound 107 | —C(NH)NH—CH₂—C₆H₄—F | OH | HBr | 264.5~267.5 |
| Compound 108 | —C(NH)NH—CH₂—C₆H₄—CF₃ | OMe | HI | 198~204 |
| Compound 109 | —C(NH)NH—CH₂—C₆H₄—CF₃ | OH | HBr | 239~240.5 |
| Compound 110 | —C(NH)NH—CH₂—(2-pyridyl) | OMe | HI | 186.5~188* |
| Compound 111 | —C(NH)NH—CH₂—(2-pyridyl) | OH | HCl | 249~250* |
| Compound 112 | —C(NH)NH—(CH₂)₂—C₆H₅ | OMe | HI | 226~228* |
| Compound 113 | —C(NH)NH—(CH₂)₂—C₆H₅ | OH | (2H₂O) | 229~232* |
| Compound 114 | —C(NH)NH—(CH₂)₂—(2-pyridyl) | OMe | HI | 202~203.5* |
| Compound 115 | —C(NH)NH—(CH₂)₂—(2-pyridyl) | OH | 2HCl | 234~235* |
| Compound 116 | —C(NH)NH—cyclopentyl | OMe | HI | 248~249 |

TABLE 4-continued

[Structure: R¹–C₆H₄–C(=O)–N=C(S...)–N(Me)–... with =C(Me)–C(=O)–NH–(CH₂)₂–COR⁴]

| Compound No. | R¹ | R⁴ | Salt | m.p. (°C.) |
|---|---|---|---|---|
| Compound 117 | —C(NH)NH—(cyclopentyl) | OH | HBr | 241~243 |
| Compound 118 | —C(NH)NH—(cyclohexyl) | OMe | HI | 226~229 |
| Compound 119 | —C(NH)NH—(cyclohexyl) | OH | HBr | 180~181 |
| Compound 120 | —C(NH)NH—(cycloheptyl) | OMe | HI | 242~245 |
| Compound 121 | —C(NH)NH—(cycloheptyl) | OH | HBr | 244~246 |
| Compound 122 | —C(NH)NH-n-Bu | OMe | HI | 212~218 |
| Compound 123 | —C(NH)NH-n-Bu | OH | HBr | 249~250 |
| Compound 124 | —C(NH)N(piperidino) | OMe | HI | 204~207 |
| Compound 125 | —C(NH)N(piperidino) | OH | HBr | 199.5~202 |
| Compound 126 | —C(NH)N(pyrrolidino) | OMe | HI | 210~212.5 |
| Compound 127 | —C(NH)N(pyrrolidino) | OH | HBr | 220~224.5 |
| Compound 128 | —C(NH)N(pyrrolidino) | OMe | HI | 180.5~183 |
| Compound 129 | —C(NH)NH—(2-MeO-C₆H₄) | OH | HBr | 186~192 |

TABLE 4-continued
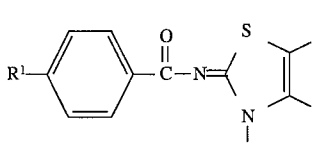
| Compound No. | R¹ | R⁴ | Salt | m.p. (°C.) |
|---|---|---|---|---|
| Compound 130 | 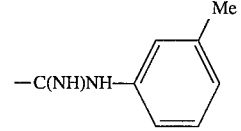 | OMe | HI | 185~188.5 |
| Compound 131 | 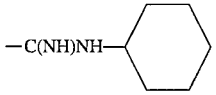 | OH | HBr | 221~224 |
*indicates decomposition in the m.p. column.
TABLE 5
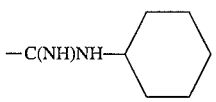
| Compound No. | R¹ | R⁴ | Salt | m.p. (°C.) |
|---|---|---|---|---|
| Compound 132 | 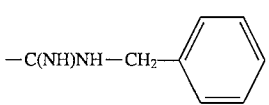 | OMe | HI | 166.5~168 |
| Compound 133 | —C(NH)NH— cyclohexyl | OH | | 189~191 |
| Compound 134 | 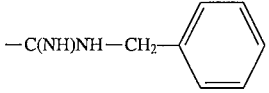 | OMe | HI | 119~120 |
| Compound 135 | —C(NH)NH—CH₂—phenyl | OH | | 181~182 |
| Compound 136 | 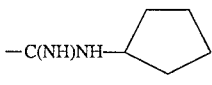 | OMe | HI | 176~180 |
| Compound 137 | 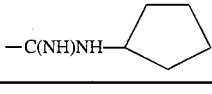 | OH | | 177~180 |

EXAMPLE 56

α-Methylthio-4-{[5-(2-(methoxycarbonyl)ethylaminocarbonyl)- 3,4-dimethyl-3H-thiazoline-2-dene]aminocarbonyl]benzylidene morpholinium iodide (0.35 g) obtained Example 53(1) was added to a solution of ammonium acetate (0.07 g) in methanol (5 ml) under heating reflux, followed by stirring for 1.5 hours. The reaction mixture was cooled, and the precipitated crystals were collected by filtration to give N-(2-methoxycarbonylethyl)- 2-[4-(morpholinoimidoyl)benzoylimino]-3,4-dimethyl-3H-thiazoline-5-carboxamide hydroiodide (Compound 138) (0.19 g).

m.p. 247°~248° C.

EXAMPLE 57

Compound 138 (0.09 g) and 23% hydrobromic acid (1 ml) were stirred at 90° C. for 3 hours. The reaction mixture was cooled, and the precipitated crystals were collected by filtration to give N-(2-carboxyethyl)-2-[ 4-(morpholinoimidoyl)benzoylimino]-3,4-dimethyl-3H-thiazoline- 5-carboxamide hydrobromide (Compound 139) (0.035 g).

m.p. 258.5°~260° C. (decomposition)

EXAMPLE 58

A mixture of Compound 3 (1.0 g), cis-2,6-dimethylmorpholine (0.41 g), acetic acid (0.22 ml) and methanol (20 ml) was heated under reflux with stirring for 90 minutes. The reaction mixture was concentrated under reduced pressure and then, the crystals were recrystallized from methylene chloride-acetone to give N-(2-methoxycarbonylethyl)-2-[4-(cis- 2,6-dimethylmorpholinoimidoyl)benzoylimino]-3,4-dimethyl-3H-thiazoline- 5-carboxamide hydroiodide (Compound 140) (0.81 g).

m.p. 231°~232.5° C. (decomposition)

EXAMPLE 59

Compound 140 (0.4 g), 10% aqueous sodium hydroxide solution (1.0 ml) and methanol (20 ml) were heated under reflux with stirring for an hour. The reaction mixture was concentrated under reduced pressure, and 3% hydrochloric acid was added thereto under ice-cooling. The precipitated crystals were collected by filtration to give N-(2-carboxyethyl)-2-[ 4-(cis-2,6-dimethylmorpholinoimidoyl)benzoylimino]- 3,4-dimethyl-3H-thiazoline-5-carboxamide monohydrate (Compound 141) (0.23 g).

m.p. 194°~200° C. (decomposition).

EXAMPLE 60

Following the procedure similar to that of Example 58 using Compound 3, if desired, and further following the procedure of that of Example 57 or 59, there were obtained the following compounds (Compounds 142~225) shown in Tables 6 and 7.

TABLE 6

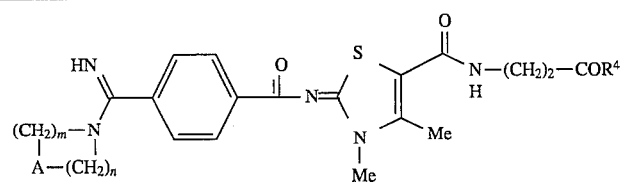

| Compound No. | m | n | A | $R^{23}$ | $R^4$ | Salt | m.p. (°C.) | |
|---|---|---|---|---|---|---|---|---|
| 142 | 1 | 2 | S | — | OMe | HI | 203~205 | * |
| 143 | 1 | 2 | S | — | OH | (2H$_2$O) | 208~212 | * |
| 144 | 2 | 2 | S | — | OMe | HI | 188~190 | * |
| 145 | 2 | 2 | S | — | OH | (3H$_2$O) | 174~178 | * |
| 146 | 2 | 2 | NR$^{23}$ | HCO | OMe | HI | 226~228 | * |
| 147 | 2 | 2 | NR$^{23}$ | HCO | OH | (3H$_2$O) | 211.5~213.5 | * |
| 148 | 2 | 2 | NR$^{23}$ | Me | OMe | HI | 233~236 | * |
| 149 | 2 | 2 | NR$^{23}$ | Me | OH | [Note 1] | 266~267 | * |
| 150 | 2 | 2 | NR$^{23}$ | Et | OMe | HI | >300 | * |
| 151 | 2 | 2 | NR$^{23}$ | Et | OH | [Note 2] | 265~266 | * |
| 152 | 2 | 2 | NR$^{23}$ | Ph | OMe | HI | 155~158 | * |
| 153 | 2 | 2 | NR$^{23}$ | Ph | OH | (H$_2$O) | 240~242 | * |
| 154 | 2 | 2 | NR$^{23}$ | 2-Me-Ph | OMe | HI | 237~239 | * |
| 155 | 2 | 2 | NR$^{23}$ | 2-Me-Ph | OH | (2H$_2$O) | 210~211.5 | * |
| 156 | 2 | 2 | NR$^{23}$ | 3-Me-Ph | OMe | HI | 181~183 | * |
| 157 | 2 | 2 | NR$^{23}$ | 3-Me-Ph | OH | (3H$_2$O) | 205~207 | * |
| 158 | 2 | 2 | NR$^{23}$ | 2-Cl-Ph | OMe | HI | 233~235 | * |
| 159 | 2 | 2 | NR$^{23}$ | 2-Cl-Ph | OH | (3H$_2$O) | 180.5~182.5 | * |
| 160 | 2 | 2 | NR$^{23}$ | 4-Cl-Ph | OMe | HI | 220~222 | * |
| 161 | 2 | 2 | NR$^{23}$ | 4-Cl-Ph | OH | (2H$_2$O) | 239~241 | * |
| 162 | 2 | 2 | NR$^{23}$ | 2-F-Ph | OMe | HI | 173~176 | * |
| 163 | 2 | 2 | NR$^{23}$ | 2-F-Ph | OH | (H$_2$O) | 219~221 | * |
| 164 | 2 | 2 | NR$^{23}$ | 4-F-Ph | OMe | HI | 216~220 | * |
| 165 | 2 | 2 | NR$^{23}$ | 4-F-Ph | OH | (2H$_2$O) | 195~197 | * |
| 166 | 2 | 2 | NR$^{23}$ | 3-CF$_3$-Ph | OMe | HI | 162~164 | * |
| 167 | 2 | 2 | NR$^{23}$ | 3-CF$_3$-Ph | OH | (H$_2$O) | 226~228 | * |
| 168 | 2 | 2 | NR$^{23}$ | 2-MeO-Ph | OMe | HI | 216~220 | * |
| 169 | 2 | 2 | NR$^{23}$ | 2-MeO-Ph | OH | (H$_2$O) | 150~152 | * |

TABLE 6-continued

Structure: HN=C(NH-(CH₂)ₘ-N(A-(CH₂)ₙ)-)-C₆H₄-C(=O)-N=C(S-C(Me)=C(-C(=O)-NH-(CH₂)₂-COR⁴)-)N(Me)

| Compound No. | m | n | A | R²³ | R⁴ | Salt | m.p. (°C.) | |
|---|---|---|---|---|---|---|---|---|
| 170 | 2 | 2 | NR²³ | 4-MeO-Ph | OMe | HI | 196~198 | * |
| 171 | 2 | 2 | NR²³ | 4-MeO-Ph | OH | (3H₂O) | 234~236 | * |
| 172 | 2 | 2 | NR²³ | 4-Ac-Ph | OMe | HI | 189~192 | * |
| 173 | 2 | 2 | NR²³ | 4-Ac-Ph | OH | (2H₂O) | 210~211 | * |
| 174 | 2 | 2 | NR²³ | 4-NO₂-Ph | OMe | HI | 231~232.5 | * |
| 175 | 2 | 2 | NR²³ | 4-NO₂-Ph | OH | [Note 3] | 183~185 | * |
| 176 | 2 | 2 | NR²³ | CH₂Ph | OMe | HI | 174~178 | * |
| 177 | 2 | 2 | NR²³ | CH₂Ph | OH | (1.5H₂O) | 278~279 | * |
| 178 | 1 | 2 | CH₂ | — | OMe | HI | 210~212.5 | |
| 179 | 1 | 2 | CH₂ | — | OH | [Note 4] | 220~224.5 | |
| 180 | 2 | 2 | CH₂ | — | OMe | HI | 204~207 | |
| 181 | 2 | 2 | CH₂ | — | OH | HBr | 199.5~202 | |
| 182 | 2 | 2 | C=O | — | OMe | HI | 224~226 | * |
| 183 | 2 | 2 | C=O | — | OH | (2H₂O) | 246~248 | * |
| 184 | 2 | 2 | O-C(-O-)(ring) | — | OMe | HI | 212~214 | * |
| 185 | 2 | 2 | O-C(-O-)(ring) | — | OH | (2H₂O) | 166~169 | * |

[Note 1] and [Note 2] indicate each HCl.(3H₂O).
[Note 3] indicates 2HBr.(3H₂O).
[Note 4] indicates HBr.(1.5H₂O).
*indicates decomposition in the m.p. column.

TABLE 7

Structure: HN=C(NH-(CH₂)ₘ-N(A-(CH₂)ₙ)-)-C₆H₄-C(=O)-N=C(S-C(Me)=C(-C(=O)-NH-(CH₂)₂-COR⁴)-)N(CH(Me)₂)

| Compound No. | m | n | A | R²³ | R⁴ | Salt | m.p. (°C.) |
|---|---|---|---|---|---|---|---|
| 186 | 2 | 2 | O | — | OMe | HI | 140~147 |
| 187 | 2 | 2 | O | — | OH | | 195~198 |
| 188 | 2 | 2 | NR²³ | 2-pyridyl | OMe | HI | 161~165 |
| 189 | 2 | 2 | NR²³ | 2-pyridyl | OH | | 219~222 |
| 190 | 2 | 2 | NR²³ | Et | OMe | HI | 123~124 |
| 191 | 2 | 2 | NR²³ | Et | OH | | 218~222 |
| 192 | 2 | 2 | NR²³ | Me | OMe | HI | 144~150 |
| 193 | 2 | 2 | NR²³ | Me | OH | | 210~212.5 |
| 194 | 2 | 2 | NR²³ | Ph | OMe | HI | 209~210.5 |
| 195 | 2 | 2 | NR²³ | Ph | OH | | 194~196 |
| 196 | 2 | 2 | NR²³ | CH₂Ph | OMe | HI | 80~80.5 |
| 197 | 2 | 2 | NR²³ | CH₂Ph | OH | | 239~239.5 |
| 198 | 2 | 2 | NR²³ | 2-Me-Ph | OMe | HI | 122~126 |
| 199 | 2 | 2 | NR²³ | 2-Me-Ph | OH | | 203~204.5 |
| 200 | 2 | 2 | NR²³ | 3-Me-Ph | OMe | HI | 199.5~200 |
| 201 | 2 | 2 | NR²³ | 3-Me-Ph | OH | | 156.5~158 |
| 202 | 2 | 2 | NR²³ | 2-Cl-Ph | OMe | HI | 92~94.5 |
| 203 | 2 | 2 | NR²³ | 2-Cl-Ph | OH | | 150~150.5 |
| 204 | 2 | 2 | NR²³ | 4-Cl-Ph | OMe | HI | 208~212 |
| 205 | 2 | 2 | NR²³ | 4-Cl-Ph | OH | | 130~130.5 |

TABLE 7-continued

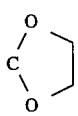

| Compound No. | m | n | A | R23 | R4 | Salt | m.p. (°C.) |
|---|---|---|---|---|---|---|---|
| 206 | 2 | 2 | NR23 | 2-F-Ph | OMe | HI | 187.5~188 |
| 207 | 2 | 2 | NR23 | 2-F-Ph | OH |  | 151.5~154 |
| 208 | 2 | 2 | NR23 | 4-F-Ph | OMe | HI | 167.5~169.5 |
| 209 | 2 | 2 | NR23 | 4-F-Ph | OH |  | 141~141.5 |
| 210 | 2 | 2 | NR6 | 3-CF3-Ph | OMe | HI | 200~201 |
| 211 | 2 | 2 | NR6 | 3-CF3-Ph | OH |  | 144~146 |
| 212 | 2 | 2 | NR6 | 2-MeO-ph | OMe | HI | 190.5~191 |
| 213 | 2 | 2 | NR6 | 2-MeO-Ph | OH |  | 125.5~126 |
| 214 | 2 | 2 | NR6 | 4-MeO-Ph | OMe | HI | 160~163 |
| 215 | 2 | 2 | NR6 | 4-MeO-Ph | OH |  | 200~204 |
| 216 | 2 | 2 | NR6 | 4-Ac-Ph | OMe | HI | 183~184.5 |
| 217 | 2 | 2 | NR6 | 4-Ac-Ph | OH |  | 183~185 |
| 218 | 2 | 2 | NR6 | 4-NO2-Ph | OMe | HI | 212~214 |
| 219 | 2 | 2 | NR6 | 4-NO2-Ph | OH |  | 186~188 |
| 220 | 2 | 2 | NR6 | HCO | OMe | HI | 113~114 |
| 221 | 2 | 2 | NR6 | HCO | OH |  | 238~238.5 |
| 222 | 2 | 2 | C=O | — | OMe | HI | 155.5~157.5 |
| 223 | 2 | 2 | C=O | — | OH |  | 109~110.5 |
| 224 | 2 | 2 |  | — | OMe | HI | 164~166 |
| 225 | 2 | 2 |  | — | OH |  | 182~184 |

EXAMPLE 61

A mixture of Compound 3 (1.5 g), 4-(pyridin- 2-yl)piperadine (0.47 g), acetic acid (0.18 ml) and methanol (20 ml) was heated under reflux for 2 hours. The reaction mixture was evaporated under reduced pressure, the residue was recrystallized from a mixture of methylene chloride and acetone to give N-(2-methoxycarbonylethyl)- 2-{4-[4-(pyridin-2-yl)piperadinyl]-imidoylbenzoylimino}-3,4-dimethyl-3H-thiazoline-5-carboxamide hydroiodide (Compound 226).

EXAMPLE 62

A mixture of Compound 226 (1.0 g), 10% sodium hydroxide solution (1.74 ml) and methanol (10 ml) was stirred at room temperature for an hour. A sodium dihydrogen phosphate solution was added to the reaction mixture, and the precipitated crystals were collected by filtration to give N-(2-carboxyethyl)-2-{4-[4-pyridin- 2-yl)piperadinyl]imidoylbenzoylimino}-3,4-dimethyl-3H-thiazoline- 5-carboxamide (Compound 227).

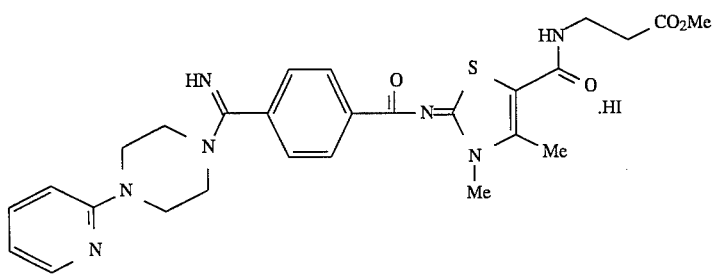

m.p. 221 ~ 223° C.

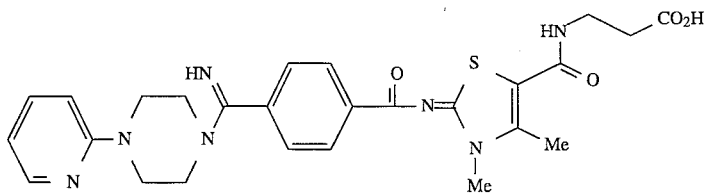

m.p. 290.5~210.5° C.

EXAMPLE 63

A mixture of Compound 61 (1.5 g), 4-(pyridin-2-yl)piperadine (0.47 g), acetic acid (0.18 ml) and methanol (20 ml) was heated under reflux for 2 hours. The reaction mixture was evaporated under reduced pressure, the residue was recrystallized from a mixture of methylene chloride and acetone to give N-methyl-N-( 2-methoxycarbonylethyl)-2-{4-[4-pyridin-2-yl)piperadinyl] -imidoylbenzoylimino}-3,4-dimethyl-3H-thiazoline-5-carboxamide hydroiodide (Compound 228).

m.p. 195°~200° C.

EXAMPLE 64

A mixture of Compound 228 (1.0 g), 10% sodium hydroxide solution (1.74 ml) and methanol (10 ml) was stirred at room temperature for an hour. 3% Hydrochloric acid was added to the reaction mixture, and after concentration under reduced pressure, the precipitated crystals were collected by filtration to give N-methyl-N-(2-carboxyethyl)-2-{4-[4-(pyridin-2-yl)piperadinyl]imidoylbenzoylimino}-3,4-dimethyl-3H-thiazoline- 5-carboxamide (Compound 229).

m.p. 243°~244° C.

What is claimed:

1. A thiazoline derivative represented by the formula:

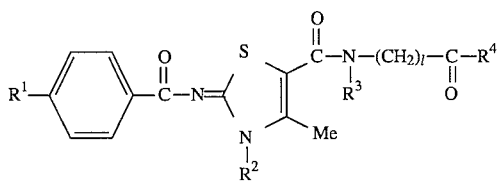

[wherein $R^1$ is (i) a cyano group,
(ii) a carbamoyl group,
(iii) a thiocarbamoyl group,
(iv) a morpholinothiocarbonyl group,
(v) an alkylthioimidoyl group having 2 to 7 carbon atoms,
(vi) a group represented by the formula:

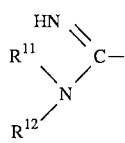

(wherein $R^{11}$ and $R^{12}$ are each a hydrogen atom, an alkyl group having 1 to 6 carbon atoms, an alkoxycarbonyl group having 2 to 7 carbon atoms, a cycloalkyl group having 4 to 8 carbon atoms, a phenyl group, a phenyl group substituted by an alkyl group having 1 to 4 carbon atoms, an alkoxy group having 1 to 4 carbon atoms or a halogen atom, an aralkyl group, or an aralkyl group substituted by an alkyl group having 1 to 4 carbon atoms, an alkoxy group having 1 to 4 carbon atoms, a trifluoromethyl group or a halogen atom), (vii) a group represented by the formula:

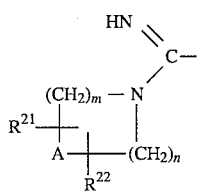

(wherein $R^{21}$ and $R^{22}$ are each a hydrogen atom or an alkyl group having 1 to 6 carbon atoms, m and n are each an integer of 1 to 3, and A is a methylene group, a carbonyl group, an ethylenedioxymethylene group, an oxygen atom, a sulfur atom, a sulfinyl group, a sulfonyl group or a group represented by the formula:

$<NR^{23}$ (wherein $R^{23}$ is a hydrogen atom, an alkyl group having 1 to 6 carbon atoms, a formyl group, an alkanoyl group having 2 to 7 carbon atoms, a phenyl group, a phenyl group substituted by an alkyl group having 1 to 6 carbon atoms, an alkoxy group having 1 to 6 carbon atoms, a nitro group, an alkanoyl group having 2 to 7 carbon atoms, a halogen atom or a trifluoromethyl group, a pyridyl group or a benzyl group)), or (viii) an imidazolin-2-yl group, $R^2$ is an alkyl group having 1 to 10 carbon atoms or an aralkyl group, $R^3$ is a hydrogen atom or an alkyl group having 1 to 4 carbon atoms, $R^4$ is a hydroxyl group, an alkoxy group having 1 to 6 carbon atoms, an alkoxy group having 1 to 6 carbon atoms substituted by a phenyl group, a pyridyl group, a morpholino group, an alkanoyloxy group having 2 to 7 carbon atoms, an alkoxy group having 1 to 6 carbon atoms, an N,N-dialkylaminocarbonyl group or an N,N-dialkylamino group, or an amino group, and l is an integer of 1 to 5] and a salt thereof.

* * * * *